United States Patent [19]

Henry

[11] Patent Number: 5,534,242

[45] Date of Patent: * Jul. 9, 1996

[54] LIDOCAINE-VASOCONSTRICTOR AEROSOL PREPARATION

[76] Inventor: Richard A. Henry, 7 Toronto Street, Kingston, Ontario, Canada, K7L 4A3

[ * ] Notice: The term of this patent shall not extend beyond the expiration date of Pat. No. 5,453,445.

[21] Appl. No.: 408,877

[22] Filed: Mar. 24, 1995

Related U.S. Application Data

[63] Continuation-in-part of Ser. No. 236,408, May 2, 1994, Pat. No. 5,453,445.

[51] Int. Cl.$^6$ ............................ A61L 9/04; A61K 31/165; A61K 31/135

[52] U.S. Cl. ............................ 424/45; 514/622; 514/653; 514/654; 514/818

[58] Field of Search ............................ 424/45; 514/626, 514/653, 654, 818

[56] References Cited

U.S. PATENT DOCUMENTS

| | | | |
|---|---|---|---|
| 5,118,494 | 6/1992 | Schultz et al. | 424/45 |
| 5,190,029 | 3/1993 | Byron et al. | 128/200.14 |
| 5,225,183 | 7/1993 | Purewal et al. | 424/45 |

OTHER PUBLICATIONS

Paul J. Atkins et al., "The Design and Development of Inhalation Drug Delivery Systems" pp. 155–185. (1992).

Folke Moren. "Aerosol dosage forms and formulations" *Aerosols in Medicine, Principles, Diagnosis and Therapy* 2nd Edition. 1993, pp. 321–350.

Michael Whitham et al. "Alternative Propellants: Proprietary Rights, Toxicological Issues and Projected Licensing Problems" *Respiratory Drug Delivery IV*, May 1–6, 1994.

Byron et al., "Some Aspects of Alternative Propellant Solvency" *Respiratory Drug Delivery IV*, May 1–6, 1994.

Dalby et al., "CFC Propellant Substitution: P–134a as a Potential Replacement for P–12 in MDIs" *Pharmaceutical Technology* Mar. 1990.

CA118:87647, Fassberg et al., 1992.

*Primary Examiner*—Kimberly Jordan
*Attorney, Agent, or Firm*—Whitham, Curtis, Whitham & McGinn

[57] ABSTRACT

Clear and stable aerosol formulations including both lidocaine base and vasoconstricting agents have been produced. This combination of medicaments are dissolved in suitable hydrofluorocarbon propellants with additional organic solvent as required. The lidocaine base serves to improve the solubility of the vasoconstricting agent and reduce the concentration of organic solvent required. This aerosol combination is designed for nasal application to cause topical anesthesia and concomitant vasoconstriction in preparation for nasal examination or instrumentation. It is also suitable for application to other anatomical sites such as the upper airway, anus and genital tract.

11 Claims, No Drawings

LIDOCAINE-VASOCONSTRICTOR AEROSOL PREPARATION

CROSS-REFERENCE TO RELATED APPLICATIONS

This application is a continuation-in-part application of the patent application filed May 2, 1994, having U.S. Ser. No. 08/236,408, now U.S. Pat. No. 5,453,445, and the complete contents of that patent application is herein incorporated by reference.

BACKGROUND OF THE INVENTION

1. Field of the Invention

The invention is generally related to aerosol formulations delivered by metered dose inhalers (MDIs). More particularly, the invention is directed to aerosol formulations which include vasoconstricting agents and the local anesthetic agent lidocaine in its base form dissolved in hydrofluorocarbon propellants.

2. Description of the Prior Art

Vasoconstriction of blood vessels is achieved by stimulation of the alpha receptors in the smooth muscle cells of the blood vessel wall. Vasoconstriction is desirable in some clinical situations both systemically to correct hypotension and locally to reduce regional blood flow. The alpha-1 adrenergic receptors, found in the smooth muscle cells of the peripheral vaculature of the coronary arteries, skin, uterus, intestinal mucosa and splanchnic beds, mediate vasoconstriction. These receptors serve as postsynaptic activators of vascular and intestinal smooth muscles as well as endocrine glands. Their activation results in either decreased or increased tone, depending upon the effector organ. The response in resistance and capacitance blood vessels is constriction. Alpha-1 adrenergic agonists include the natural catecholamines, epinephrine, norepinephrine and dopamine, and the synthetic noncatecholamines such as ephedrine, mephentermine, amphetamines, metaraminol, phenylephrine and methoxamine.

Phenylepherine is considered a potent pure alpha-1 agonist drug which increases venous as well as arterial constriction. Phenylephrine is used intravenously in small doses of approximately 1 μg/kg body weight to cause systemic vasoconstriction and elevation of blood pressure. It is also used regionally to cause vasoconstriction when injected with local anesthetic agents to provide prolonged nerve conduction block.

Phenylephrine has been found to provide excellent decongestion of the nasal mucosa by exerting its alpha-1 mediated vasoconstricting effect on the mucosal blood vessels. This directly opposes the histamine-mediated vasodilation and reduces mucosal oedema and vascularity. Other agents that have been used for this effect are ephedrine and cocaine.

Cocaine possesses both anesthetic and vasoconstricting properties. These properties make it suitable to provide both topical anesthesia and vasoconstriction of the nasal mucosa to improve patient tolerance of nasal catheterization during nasotracheal intubation, nasogastric tube insertion, or fiberoptic examination of the nose. Vasoconstriction results in shrinking of the nasal mucosa with enlargement of the nasal passage and reduced bleeding during nasal procedures.

Although cocaine provides good vasoconstriction and is well tolerated by most patients, there are significant problems with its use. One such problem is that even small doses (approximately 30 mg for example) may cause systemic toxicity. Another problem relates to the potential diversion and illicit use of cocaine by medical personnel. The handling and storage of controlled substances involves additional administrative costs and risks.

Lidocaine is similar to cocaine in effectiveness as a local anesthetic, but it does not vasoconstrict the mucosa and thus dilate the nasal passage. For this reason, phenylephrine has been combined with lidocaine to reduce nasal congestion. The combination of lidocaine and phenylephrine has been advocated as an alternative to cocaine and its efficacy evaluated in a number of studies.

Currently, lidocaine and phenylephrine are required to be mixed by the clinician before applying the solution. Suitable recommended combinations are 3–4% lidocaine hydrochloride in water mixed with 0.25–1% phenylephrine hydrochloride, also in water. The aqueous solution is then delivered to nasal mucosa as a spray using a conventional manual atomizer or a multi-orificed cannula and syringe delivery system. The optimum dose used with this spray application is 1.25–1.5 mg phenylephrine hydrochloride and 12–15 mg lidocaine hydrochloride per nostril of adult patients.

The methods of delivery and efficacy of lidocaine and phenylephrine are discussed and evaluated in the following studies: Curtis N. Sessler et al., *Anesthesiology* 64:274–277 (1986); Jeffrey Gross et al., *Anesthesia & Analgesia* 63:915–918 (1984); and Robert M. Middleton et al., *Chest* 99:5:1093–1096 (1991).

Drug deposition in the nasal cavity is reviewed in Volume 39 of the "Drugs and the Pharmaceutical Sciences" series titled *Nasal Systemic Drug Delivery*, edited by Yie W. Chien, Kenneth S. E. Su and Shyi-Feu Cheng and published by Marcel Dekker, Inc. in 1989.

"The deposition of aerosols in the respiratory tract is a function of particle size and respiratory patterns. The density, shape and hygroscopicity of the particles and the pathological conditions in the nasal passage will influence the deposition of particles, whereas the particle size distribution will determine the site of deposition and affect the subsequent biological response in experimental animals and man."

"A uniform distribution of particles throughout the nasal mucosa could be achieved by delivering the particles from a nasal spray using a pressurized gas propellant."

Factors related to the dosage form of the drug found to affect the pharmacokinetics of nasal absorption include concentration of active drug, physiological properties of active drug, density/viscosity properties of the formulation, pH/toxicity of dosage form, and pharmaceutical excipients used.

Highly concentrated drugs which are lipid soluble at nasal pH of 5.5 to 6.6 and, when dissolved in a minimal amount of excipient, will be rapidly and extensively absorbed.

Lidocaine base is freely lipid soluble and will cross mucous membranes readily. It is insoluble in water and thus not suitable for use in an aqueous suspension, requiring ethanol or the like to obtain a liquid solution. Some way to produce a fine spray of lidocaine base would be advantageous for delivery to the nose.

Vasoconstricting agents such as phenylephrine are usually used in their salt forms which are water soluble and thus suitable for intravenous injection.

MDIs have been used extensively and have proven to be an effective means of producing a reproducible preselected dose of medicament in a predictable spray pattern and droplet size. This is particularly advantageous when delivering potent drugs where the need for reliable drug delivery is important and where overdoseage leads to dangerous clinical side-effects.

A problem with the use of MDIs relates to the chlorofluorocarbon (CFC) propellants which have been used in MDIs. All chlorine-containing halohydrocarbons have been implicated in the destruction of the earth's ozone layer with subsequent adverse effects on human and animal life. Worldwide treaties have called for a ban on these propellants due to their alleged impact on the earth's ozone layer. The most widely recognized CFC alternatives are hydrofluorocarbon (HFC) propellants, such as 1,1,1,2-tetrafluoroethane and 1,1,1,2,3,3,3-heptafluoropropane, and these propellants have been readily adopted in the refrigeration, polymer foam blowing, and electronic cleaning industries. However, HFC propellants have been found to behave differently than CFC propellants in the MDI environment. In particular, it has been found to be very difficult to solubilize or disperse pharmaceuticals in HFCs. Without solubilization or uniform dispersability in the propellant, the MDI cannot provide a reproducible and efficacious dose of medicament. Much work has been performed in the area of designing new surfactants and identifying co-solvents that can be used to solubilize or disperse pharmaceuticals in HFC propellants.

To date, no MDI pharmaceutical products that utilize HFC propellants have been approved for use by any industrialized country. Although, reports on recent submissions to regulatory agencies suggest that 1,1,1,2-tetrafluoroethane and 1,1,1,2,3,3,3-heptafluoroethane based MDIs are the most likely CFC-alternative MDIs to gain approval in the near future.

The object of aerosolized medication delivery by MDI is to provide the medicament in stable suspension or solution form in the propellant in a suitable concentration for clinical effect, with minimal or no additives. The droplet size is predictable and is a function of the suspended particle size in a suspension formulation or the relative volume of drug and its cosolvents to the propellant volume in a solution formulation. The propellant should constitute at least about 45% of the total formulation weight and preferably about 60–98% of the formulation weight.

Lidocaine and phenylephrine have been shown to exert independent effects on the nasal mucosa that result in vasoconstriction and topical anesthesia. Both of these effects have been found to be helpful during procedures involving manipulation or examination of the nose. The clinical effect is similar and considered superior in efficacy to cocaine, but the need to premix the solution and also to provide a suitable way to deliver a solution or suspension thereof has prevented their combined use from gaining universal acceptance as well as from being employed for all nasal manipulations such as nasogastric tube insertion, where its use should be advantageous to the patient.

Other clinical situations where a combined lidocaine/vasoconstricting agent formulation, such as lidocaine/phenylephrine, would be in providing topical anesthesia and vasoconstricting in the upper airway, open skin wounds, the urethra, anus, and the cervix and vagina.

The present invention provides a solution to this longstanding shortcoming or deficiency of the art.

SUMMARY OF THE INVENTION

An object of this invention is to provide novel formulations of lidocaine and topically acting vasoconstricting agents suitable for use in an MDI.

Another object of this invention is to provide an MDI formulation which includes one or more HFC propellants that includes lidocaine in its lipid-soluble free base form and one or more vasoconstricting agents.

Yet another object of this invention is to provide a method of solubilizing vasoconstricting agents in HFC propellants wherein the lidocaine is used to both improve the absorption of vasoconstricting agents into the HFC propellants.

Still another object of this invention is to provide compositions incorporating vasoconstricting agents, such as phenylephrine, as stable, pharmacologically acceptable acid addition salts such s hydrochloride or bitartrate salts, dissolved in suitable solvents in an HFC propellant.

According to the invention, vasoconstricting agents, such as phenylephrine, ephedrine, epinephrine, norepinephrine, dopamine, pseudo-ephedrine, mephentermine, amphetamines, metaraminol, methoxamine, phenylpropanolamine, B-hydroxyphenethylamine, 3,4-dihydroxynorephedrine, etc. have been found to be more easily dissolved in therapeutic concentrations in HFC propellants such as 1,1,1,2-tetrafluoroethane (HFC-134a) and 1,1,1,2,3,3,3-heptafluoropropane (HFC-227), when lidocaine free base is added. Experiments have shown that solubility of the vasoconstricting agents can be achieved with less organic solvent when lidocaine base is present than is possible in the absence of lidocaine base. An example of this is phenylephrine hydrochloride and ethyl alcohol where almost 50% more ethyl alcohol is required to maintain a solution of phenylephrine hydrochloride in HFC-134a in the absence of lidocaine base. Examples of organic solvents considered useful in these formulations are ethyl alcohol, benzyl alcohol, propylene glycol, diethyl ether, dimethoxyethane, etc. Some of these solvents are not soluble when lidocaine base is present. Some of the vasoconstricting agents, such as ephedrine, which do not have hydroxyl groups on the benzene ring structure, have been found to have limited solubility in the HFC propellant alone. The addition of lidocaine base improved the solubility of these agents to allow therapeutic concentrations to be achieved. In essence, the lidocaine base is acting as both a solubilizing agent as well as a thereapeutic agent in aerosol formulations prepared with vasoconstricing agents.

DETAILED DESCRIPTION OF THE PREFERRED EMBODIMENTS OF THE INVENTION

Vasoconstricting agents, such as phenylephrine hydrochloride, have been found to be insoluble in HFC propellants such as HFC-134a and HFC-227. In addition, when the vasoconstricting agents were dissolved in EtOH in clinically useful concentrations (e.g., approximately 2.0–2.5%) and then mixed with HFC-134a or HFC-227, the vasoconstricting agents precipitated out of solution in the alcohol.

Lidocaine base has been found to be extremely soluble in HFC propellants. Table 1 shows the solubility of lidocaine base in selected media.

TABLE 1

| Propellant | Solubility Weight % | mg/ml |
| --- | --- | --- |
| HFC-134a | 58 | 759 |
| HFC-227 | 45 | 602 |
| Water | 0 | 0 |

Vasoconstricting agents such as phenylephrine are usually used in their salt forms which are water soluble and thus suitable for intravenous injection. These agents are very potent and rapid acting and the base form is not considered to be a major clinical advantage in this formulation, but where improved solubility of the base form is shown, the base is preferred.

When the vasoconstricting agents were combined with lidocaine base and the HFC propellant, they were found to be either more soluble or soluble with proportionally less organic solvent to keep them in a stable solution. These observations demonstrate that the lidocaine acts as an adjuvant to assist and maintain the solubility of the vasoconstricting agents. Thus, this invention particularly contemplates using lidocaine base in solution in HFC propellants such as HFC-134a or HFC-227 or combinations thereof, to more readily dissolve pharmacologically active concentrations of vasoconstricting agents, such as phenylephrine, in the HFC propellants with either no organic solvent requirement for the formulation or significantly less organic solvent than would be required if no lidocaine were present.

The Example section below demonstrates that different vasoconstricting agents can be solubilized into HFC propellants using lidocaine base. In addition, the Example section shows that several different organic solvents which are not soluble in HFC propellants, can be made soluble when combined with lidocaine base. Moreover, the Example section demonstrates that vasoconstricting agents may be dissolved in HFC propellants without an organic solvent and using lidocaine base solely as a solubilizing agent.

Preferably, an aerosol formulation according to this invention will comprise lidocaine free base at 1–30% by weight, vasoconstricting agent at 0.01–10% by weight, and HFC propellant or propellant blend at 45–99% by weight. Most preferably, the lidocaine free base will be present at 5–20% by weight, the vasoconstricing agent will be present at 0.01–2% by weight, and the HFC propellant or propellant blend will be present at 60–98% by weight. Solvents such as ethanol (EtOH or ethyl alcohol), benzyl alcohol, propylene glycol, polyethylene glycol, diethylether, and dimethoxyethane may be included in the formulation. Preferably, the solvent will comprise between 1–40% w/w of the formulation, and most preferably between 1–20% w/w. Other constituents such as valve lubricants (e.g., polyethylene glycol, sorbitan trioliate, lecithin, glycerol trioleate, etc.), preservatives (e.g., benzalkonium chloride, cetyl pyridinium chloride, etc.), and the like may also be included, and preferably would constitute less than 20% w/w of the formulation. The vasoconstricting agents which may be solubilized by this include phenylephrine, ephedrine, epinephrine, norepinephrine, dopamine, 3,4-dihydroxynorephedrine, pseudo-ephedrine, mephentermine, amphetamines, metaraminol, methoxamine, phenylpropanolamine, B-hydroxyphenethyl amine, etc., and these agents can be included in the formulation in salt form (e.g., hydrochloride salt, bitartrate salt, tris salt, etc.) or base form or any other pharmocologically acceptable derivative. The metered dose inhaler in which the formulation is packaged will preferably deliver small quantities of drug per actuation (e.g., 25–100 µl doses), wherein each action will dispense approximately 1–20 mg of lidocaine free base and 0.01–1 mg of vasoconstricting agent. Most preferably, a dose of 2.5–10 mg lidocaine base and 0.05–0.2 mg vasoconstricting agent will be delivered per actuation.

An inhalable metered dose dispensable lidocaine and vasoconstricting agent combination provides excellent delivery to the nose and upper airway causing rapid onset of topical anesthesia and intense vasoconstriction of the mucous membrane targeted. This is advantageously achieved when preparing a patient's nose for examination or for passing a nasogastric feeding tube or a nasotracheal breathing tube. This drug combination delivery system is also advantageous in the acute treatment of upper airway oedema, swelling and bleeding as may occur in the presence of acute epiglottitis, inflammation, anaphylaxis and glottic tumors, etc. Additional uses can include topical application of prolapsed hemmorrhoids where topical anesthesia and vasoconstriction are the desired therapeutic goals. Further, application to the labia, vaginal mucosa, cervix and uterine endometrium will advantageously provide excellent topical anesthesia and reduced bleeding in the treatment of local lesions or in the preparation for therapeutic procedures such as cervical dilation and uterine curretage.

Manufacturing of MDI solution formulations is considered easier and cheaper than suspension formulations. Solution formulations do not require prior micronization of the delivered medicament to the desired particle size. Expensive surfactants are not required, thus reducing the patient's exposure to potentially irritant and harmful substances.

The formulations of this invention can be manufactured in different ways. In one method, the lidocaine and vasoconstricting agent are dissolved in the organic solvent and place in the aluminum canister which is then capped and pressure filled with propellant. Where an organic solvent is not required, the lidocaine and vasoconstricting agent are dissolved in the propellant which is then pressure filled into the closed empty aluminum canister. The stability and ready solubility of these solutions allow for a variety of organic solvents and filling techniques to be used.

EXAMPLE

Lidocaine USP in free base form, of the formula 2-(diethylamino)-2',6'-acetoxylidide [137-58-6] $C_{14}H_{22}N_2O$ (MW 234.34), was obtained from Astra Pharmaceutcals, Inc., in Mississuage, Ontario, Canada.

Phenylepherine hydrochloride of the formula (R)-3-hydroxy-alpha-[(methylamino)methyl]benzene methanol hydrochloride $C_9H_{14}ClNO_3$ (MW 203.67), as well as the other chemicals, including ephedrine, metaraminol, methoxyamine, diethylene glycol, benzyl alcohol, and propylene glycol were obtained from Sigma Chemicals.

The aerosol propellants used in the formulations were HFC-134a, available from the E. I. du Pont de Nemours and Company under their trademark Dymel®, and HFC-227 supplied by Great Lakes Chemical under their trademark FM 200®. Both propellants are nonflammable vapor at room temperature and atmospheric pressure. Neither contains chlorine atoms and, as such, neither are implicated in stratospheric ozone destruction by chlorofluorocarbons or other chlorinated hydrocarbons.

In a comparative test, phenylephrine hydrochloride was dissolved in ethyl alcohol to produce a 2.5% w/w solution. This solution was placed in a glass bottle designed for pressure filling with liquid propellant. When HFC-134a was added to this solution, the phenylephrine hydrochloride was precipitated out of solution. In contrast, using the same phenylephrine hydrochloride in ethanol solution but where the solution also contained lidocaine free base, both the lidocaine base and the phenylephrine hydrochloride remained in solution after the addition of HFC-134a. This comparative test demonstrates that lidocaine is a useful adjuvant for solubilizing vasoconstricting agents such as phenylephrine in HFC-134a.

Several formulations have been prepared which demonstrate the utility and advantages of the invention. These formulations are presented for exemplary purposes only and by no means limit the scope and content of the invention defined by the claims.

| Formulation 1 | | |
|---|---|---|
| Phenylephrine hydrochloride | 43 mg | 0.86% w/w |
| Lidocaine free base | 350 mg | 7.0% w/w |
| Ethanol (density 0.81 g/ml) | 1650 mg | 33.0% w/w |
| HFC-134a (density 1.22 g/ml) | 2957 mg | 59.14% w/w |
| Formulation 2 | | |
| Phenylephrine hydrochloride | 25 mg | 0.5% w/w |
| Lidocaine free base | 500 mg | 10.0% w/w |
| Ethanol | 1000 mg | 20.0% w/w |
| HFC-134a | 3475 mg | 69.5% w/w |
| Formulation 3 | | |
| Phenylephrine hydrochloride | 40 mg | 0.8% w/w |
| Lidocaine free base | 1000 mg | 20.0% w/w |
| Ethanol | 1550 mg | 31.0% w/w |
| HFC-134a | 2410 mg | 48.2% w/w |
| Formulation 4 | | |
| Phenylephrine base | 17 mg | 0.37% w/w |
| Lidocaine free base | 229 mg | 5.0% w/w |
| Ethanol | 767 mg | 16.7% w/w |
| HFC-134a | 3576 mg | 77.93% w/w |

Formulations 1–4 were all stable formulations which had and maintained both the lidocaine free base and the phenylephrine in solution. Formulations 1–4 show that small quantities of lidocaine are very effective at solubilizing phenylephrine in HFC-134a, and that the solubilizing property was not affected by whether the phenylephrine was in hydrochloride salt or base form. Formulations which include alternative acid addition salts (bitartrate, tris, etc.) of phenylephrine, as well as other derivatives of phenylephrine will also provide satisfactory results.

| Formulation 5 | | |
|---|---|---|
| Phenylephrine hydrochloride | 32 mg | 0.64% w/w |
| Lidocaine free base | 320 mg | 6.4% w/w |
| Ethanol | 1600 mg | 32.0% w/w |
| HFC-227 | 3048 mg | 60.96% w/w |

Formulation 5 was a stable formulation which maintained both phenylephrine and lidocaine in solution. Formulation 5 demonstrates that lidocaine free base can be effectively used to solubilize phenylephrine in a different HFC propellant from that used in formulations 1–4. Specifically, formulation 5 demonstrates the use of lidocaine free base to solubilize phenylephrine in HFC-227. Lidocaine free base should be effective in solubilizing other compounds in other HFC propellants, as well as combinations of HFC propellants.

| Formulation 6 | | |
|---|---|---|
| Ephedrine base | 9 mg | 0.8% w/w |
| HFC-134a | 1104 mg | 99.2% w/w |
| maximum solubility | | |
| Formulation 7 | | |
| Ephedrine base | 29 mg | 6.9% w/w |
| Lidocaine base | 133 mg | 31.0% w/w |
| HFC-134a | 260 mg | 62.1% w/w |
| Solubilized | | |

Formulations 6 and 7 show that lidocaine base can be used to improve the solubility of vasoconstrictive agents other than phenylephrine in HFC-134a. In addition, contrasting Formulations 6 and 7, it can be seen that some vasoconstrictive agents can be solubilized in HFC-134a without other co-solvents being present (e.g., no ETOH, etc.)

| Formulation 8 | | |
|---|---|---|
| Phenylephrine hydrochloride | 1 mg | 0.02% w/w |
| Lidocaine base | 40 mg | 0.8% w/w |
| Benzyl alcohol | 219 mg | 4.3% w/w |
| HFC-134a | 4,753 mg | 94.88% w/w |

Benzyl alcohol and phenylephrine hydrochloride was not soluble in HFC-134a. Phenylephrine hydrochloride remained in solution in the benzyl alcohol, but the alcohol was not soluble in HFC-134a. However, with the addition of lidocaine as shown in formulation 8, a clear and stable solution in HFC-134a was formed. The stability of Formulation 8 demonstrates that organic solvents other than ethyl alcohol can be used in conjunction with lidocaine to solubilize vasoconstrictive agents.

| Formulation 9 | | |
|---|---|---|
| Phenylephrine hydrochloride | 3 mg | 0.14% w/w |
| Lidocaine base | 150 mg | 7.3% w/w |
| Diethylene glycol | 102 mg | 5.1% w/w |
| HFC-134a | 1775 mg | 87.46% w/w |

Diethylene glycol, like benzyl alcohol, was not readily soluble in HFC-134a. While phenylephrine hydrochloride was soluble in diethylene glycol, the combination was not soluble when combined with HFC-134a. However, the addition of lidocaine base, as shown in Formulation 9, produces a clear and stable solution of the phenylephrine hydrochloride/diethylene glycol/lidocaine base/HFC-134a formulation. Clear and stable solutions also resulted when phenylephrine base was substituted for phenylephrine hydrochloride in formulation 9. Thus, formulation 9 shows another example of an organic solvent/vasoconstrictive agent combination which can become soluble in HFCs when lidocaine base is used as an adjuvant.

| Formulation 10 | | |
|---|---|---|
| Phenylephrine hydrochloride | 3 mg | 0.44% w/w |
| Lidocaine base | 80 mg | 11.46% w/w |
| propylene glycol | 69 mg | 9.88% w/w |
| HFC-134a | 546 mg | 78.22% w/w |

Like diethylene glycol and benzyl alcohol, propylene glycol also was not soluble in HFC-134a. While phenylephrine hydrochloride was soluble in propylene glycol, the combination was not soluble when combined with HFC-134a. However, the addition of lidocaine base, as shown in Formulation 10, produces a clear and stable solution of the phenylephrine hydrochloride/propylene glycol/lidocaine base/HFC-134a formulation.

| Formulation 11 | | |
|---|---|---|
| Methoxamine base | 17 mg | 0.6% w/w |
| Lidocaine base | 92 mg | 3.3% w/w |
| Ethanol | 144 mg | 5.2% w/w |
| HFC-134a | 2351 mg | 90.9% w/w |

-continued

Formulation 12

| | | |
|---|---|---|
| Phenylpropanolamine base | 35 mg | 0.9% w/w |
| Lidocaine base | 350 mg | 9.1% w/w |
| Ethanol | 191 mg | 4.9% w/w |
| HFC-134a | 3261 mg | 85.1% w/w |

Formulations 11 and 12 show that methoxamine and phenylpropanolamine both in base form dissolved in ethanol are readily soluble in a lidocaine base/HFC-134a solution.

While the invention has been described in terms of its preferred embodiments, those skilled in the art will recognize that the invention can be practiced with modification within the spirit and scope of the appended claims.

We claim:

1. An aerosol-dispensable pharmaceutical composition, comprising:
   lidocaine base present in an amount ranging between 1–30% by weight;
   a vasoconstricting agent present in an amount ranging between 0.01–10% by weight;
   a hydrofluorocarbon propellant present in an amount ranging between 45–99% by weight, said lidocaine base and said vasoconstricting agent being dissolved in said hydrofluorocarbon.

2. The aerosol-dispensable pharmaceutical composition of claim 1 wherein said lidocaine base is present in an amount ranging between 5–20% by weight.

3. The aerosol-dispensable pharmaceutical composition of claim 1 wherein said vasoconstricting agent is selected from the group consisting of ephedrine, epinephrine, norepinephrine, dopamine, pseudo-ephedrine, mephentermine, amphetamines, metaraminol, methoxamine, phenylpropanolamine, and B-hydroxyphenethyl amine.

4. The aerosol-dispensable pharmaecutical composition of claim 1 wherein said vasoconstricting agent is present in an amount ranging between 0.01–2% by weight.

5. The aerosol-dispensable pharmaecutical composition of claim 1 wherein said hydrofluorocarbon propellant is selected from the group consisting of 1,1,1,2-tetrafluoroethane and 1,1,1,2,3,3,3-heptafluoropropane.

6. The aerosol-dispensable pharmaecutical composition of claim 1 wherein said hydrofluorocarbon propellant is present in an amount ranging between 60–98% by weight.

7. The aerosol-dispensable pharmaceutical composition of claim 1 further comprising an organic solvent present in an amount ranging between 1–40% by weight.

8. The aerosol-dispensable pharmaceutical composition of claim 7 wherein said organic solvent is selected from the group consisting of ethanol, propylene glycol, benzyl alcohol, polyethylene glycol, diethylether, and dimethoxyethane.

9. The aerosol-dispensable pharmaceutical composition of claim 7 wherein said organic solvent is present in an amount ranging between 1–20% by weight.

10. A method of solubilizing vasoconstrictive agents in hydrofluorocarbon propellants, comprising the steps of:
    combining a vasoconstrictive agent and a hydrofluorocarbon propellant; and
    solubilizing said vasoconstrictive agent in said hydrofluorocarbon propellant using lidocaine base as a solubilizing agent.

11. The method of solubilizing recited in claim 10 wherein said combining step includes the step of adding an organic solvent together with said vasoconstrictive agent and said hydrofluorocarbon propellant, and wherein said solubilizing step includes the step of solubilizing said organic solvent in said hydrofluorocarbon propellant using lidocaine base as a solubilizing agent.

\* \* \* \* \*